(12) United States Patent
Yamaji et al.

(10) Patent No.: US 11,957,509 B2
(45) Date of Patent: Apr. 16, 2024

(54) DIAGNOSIS ASSISTANCE DEVICE, DIAGNOSIS ASSISTANCE SYSTEM, AND DIAGNOSIS ASSISTANCE METHOD

(71) Applicant: TERUMO KABUSHIKI KAISHA, Tokyo (JP)

(72) Inventors: Kyohei Yamaji, Fukuoka (JP); Koichi Inoue, Kanagawa (JP); Hijiri Shimizu, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 27 days.

(21) Appl. No.: 17/692,898

(22) Filed: Mar. 11, 2022

(65) Prior Publication Data

US 2022/0192631 A1 Jun. 23, 2022

Related U.S. Application Data

(63) Continuation of application No. PCT/IB2020/059739, filed on Oct. 16, 2020.

(30) Foreign Application Priority Data

Sep. 12, 2019 (JP) ................. 2019-166485

(51) Int. Cl.
*A61B 8/12* (2006.01)
*A61B 8/00* (2006.01)
*A61B 8/08* (2006.01)

(52) U.S. Cl.
CPC .............. *A61B 8/12* (2013.01); *A61B 8/0841* (2013.01); *A61B 8/085* (2013.01); *A61B 8/4494* (2013.01); *A61B 8/461* (2013.01); *A61B 8/54* (2013.01)

(58) Field of Classification Search
CPC ......... A61B 8/12; A61B 8/0841; A61B 8/085; A61B 8/4494; A61B 8/461; A61B 8/54;
(Continued)

(56) References Cited

U.S. PATENT DOCUMENTS

2012/0310086 A1 12/2012 Fukumoto et al.
2013/0046168 A1* 2/2013 Sui ....................... A61B 8/0891
600/407
(Continued)

FOREIGN PATENT DOCUMENTS

JP 2009028096 A 2/2009
JP 2010075616 A 4/2010
(Continued)

OTHER PUBLICATIONS

The extended European Search Report dated Sep. 2, 2022, by the European Patent Office in corresponding European Patent Application No. 20863574.8-1126. (7 pages).
(Continued)

*Primary Examiner* — Baisakhi Roy
*Assistant Examiner* — Kaitlyn E Sebastian
(74) *Attorney, Agent, or Firm* — BUCHANAN INGERSOLL & ROONEY PC

(57) ABSTRACT

A diagnosis assistance device includes a control unit that generates line data indicating an intensity value of a reflected wave from an object, which is present in a transmission direction of ultrasound, for each combination of a movement position of an ultrasound transducer that radially transmits the ultrasound while being moved inside a biological tissue and the transmission direction of the ultrasound with reference to an observation result of a cross section of the biological tissue by the ultrasound transducer and generates a detection image which includes pixels corresponding to the generated line data and in which pixels
(Continued)

corresponding to the line data at the same movement position are arranged in one direction. Pixels corresponding to the line data in the same transmission direction are arranged in a direction perpendicular to the one direction, and each pixel value is set according to an abnormality degree of the generated line data.

17 Claims, 11 Drawing Sheets

(58) Field of Classification Search
CPC ..... A61B 8/5223; A61B 8/468; A61B 8/4461; A61B 8/0891; A61B 8/463; A61B 8/465; A61B 8/466; A61B 8/483; A61B 8/5207; A61B 8/0883; A61B 8/44; A61B 8/5215
See application file for complete search history.

(56) References Cited

U.S. PATENT DOCUMENTS

| | | | |
|---|---|---|---|
| 2014/0100442 A1* | 4/2014 | Begin | A61B 5/02007 600/414 |
| 2014/0100449 A1* | 4/2014 | Begin | A61B 8/0841 600/424 |
| 2015/0320317 A1 | 11/2015 | Furuichi et al. | |
| 2015/0371382 A1 | 12/2015 | Furuichi et al. | |
| 2016/0206267 A1 | 7/2016 | Shimizu et al. | |

FOREIGN PATENT DOCUMENTS

| | | |
|---|---|---|
| JP | 2015-532860 A | 11/2015 |
| JP | 2016-503310 A | 2/2016 |
| WO | 2011099102 A1 | 8/2011 |
| WO | 2014115182 A1 | 7/2014 |
| WO | 2014136137 A1 | 9/2014 |
| WO | 2015045368 A1 | 4/2015 |
| WO | 2016140116 A1 | 9/2016 |

OTHER PUBLICATIONS

Office Action (Notice of Reasons for Refusal) dated Dec. 20, 2022, by the Japan Patent Office in corresponding Japanese Patent Application No. 2019-166485 and an English translation of the Office Action. (6 pages).

International Search Report (PCT/ISA/210) with translation and Written Opinion (PCT/ISA/237) dated Dec. 22, 2020, by the Japan Patent Office as the International Searching Authority for International Application No. PCT/IB2020/059739.

* cited by examiner

DIAGNOSIS ASSISTANCE DEVICE, DIAGNOSIS ASSISTANCE SYSTEM, AND DIAGNOSIS ASSISTANCE METHOD

CROSS-REFERENCES TO RELATED APPLICATIONS

This application is a continuation of International Application No. PCT/IB2020/059739 filed on Oct. 16, 2020 (and for which the right of priority was restored), which claims priority based on Japanese Patent Application No. 2019-166485 filed on Sep. 12, 2019, the entire content of both of which is incorporated herein by reference.

TECHNOLOGICAL FIELD

The present disclosure relates to a diagnosis assistance device, a diagnosis assistance system, and a diagnosis assistance method.

BACKGROUND DISCUSSION

International Patent Application Publication No. 2014/115182 discloses a technique related to OFDI or OCT that acquires an image of a blood vessel lumen using a catheter in which an imaging core for transmitting and receiving light is provided at the tip so as to be rotatable and movable in an axial direction. The "OFDI" is an abbreviation of optical frequency domain imaging. The "OCT" is an abbreviation of optical coherence tomography.

SUMMARY

In a stent treatment for bifurcation lesions, the OFDI is useful for evaluating the narrowing and dissociation of a side branch ostium of a bifurcation and the deformation of a stent after side branch dilation. In a case in which a stent strut crossed over at the side branch ostium is expanded with a balloon in single stenting to the main branch, it is possible to reduce the deformation of the stent and the retention of the strut by passing a guide wire inserted into the side branch from the distal side of the ostium. In the OFDI, a function of forming three-dimensional images of blood vessels, stents, and guide wires makes it possible to check whether the guide wire is properly passing through the distal part. This function makes the OFDI extremely useful in understanding the anatomical information on the vascular lumen at the ostium, the running of a side branch wire, and the deformation of the stent strut caused by posterior dilation in the stent treatment for bifurcation lesions.

In the stent treatment, IVUS that acquires an image of a blood vessel lumen using a catheter in which an imaging core for transmitting and receiving ultrasound is provided at the tip so as to be rotatable and movable in an axial direction is also widely used. The "IVUS" is an abbreviation of intravascular ultrasound.

In the OFDI, blood cells in blood vessels are impeditive. Therefore, it is necessary to flush the inside of the blood vessel with, for example, a contrast medium in order to remove the blood cells. On the other hand, in the IVUS, it is usually possible to acquire an image without flushing the inside of the blood vessel. When the inside of the blood vessel is not flushed, it is possible to suppress the use of the contrast medium which is a burden on the kidneys. However, since the blood cell with a brightness value equal to or greater than a predetermined value is included in the image, it is not possible to create an image, in which the state of the guide wire and the stent strut can be observed, with the same method as that in the OFDI.

The diagnosis assistance device, system and method disclosed here make it possible to generate an image, in which the state of an object to be detected can be observed, from an observation result of a cross section of a biological tissue by ultrasound.

According to an aspect of the present disclosure, there is provided a diagnosis assistance device including: a control unit that generates line data indicating an intensity value of a reflected wave from a reflection object, which is present in a transmission direction of ultrasound, for each combination of a movement position of an ultrasound transducer that radially transmits the ultrasound while being moved inside a biological tissue and the transmission direction of the ultrasound with reference to an observation result of a cross section of the biological tissue by the ultrasound transducer and generates a detection image which includes pixels corresponding to the generated line data and in which the pixels corresponding to the line data at the same movement position are arranged in one direction, the pixels corresponding to the line data in the same transmission direction are arranged in a direction perpendicular to the one direction, and each pixel value is set according to a degree of abnormality of the generated line data.

As an embodiment of the present disclosure, the control unit calculates a degree of abnormality of a feature vector indicating features of the line data as the degree of abnormality of the line data.

As an embodiment of the present disclosure, the control unit generates, as the line data, data indicating an intensity value distribution of the reflected wave in the transmission direction of the ultrasound.

As an embodiment of the present disclosure, the control unit refers to a cross-sectional image having a brightness value distribution corresponding to the intensity value distribution as the observation result of the cross section of the biological tissue.

As an embodiment of the present disclosure, the control unit converts the intensity value distribution into a distribution from a center of gravity of the cross section observed by the ultrasound transducer and generates data indicating the converted distribution as the line data.

As an embodiment of the present disclosure, the feature vector is a vector indicating the intensity value distribution.

As an embodiment of the present disclosure, the feature vector is a vector indicating a frequency distribution of intensity of the reflected wave in the transmission direction of the ultrasound which is calculated from the intensity value distribution.

As an embodiment of the present disclosure, the feature vector is a vector that is calculated using a change in the intensity value distribution caused by a difference in the movement position of the ultrasound transducer.

As an embodiment of the present disclosure, the feature vector is a vector that is calculated using a change in the intensity value distribution caused by a difference in the transmission direction of the ultrasound.

As an embodiment of the present disclosure, the control unit compares the feature vector with an identification vector for identifying an object to be detected and calculates the degree of abnormality of the feature vector as a result of the comparison.

As an embodiment of the present disclosure, the control unit calculates the degree of abnormality of the feature vector using at least two different vectors as the identification vector and sets at least two of an R value, a G value, and a B value according to the degree of abnormality calculated using different vectors when setting an RGB value of each pixel as each pixel value of the detection image.

As an embodiment of the present disclosure, when setting the RGB value of each pixel as each pixel value of the detection image, the control unit sets one or two of the R value, the G value, and the B value according to statistics of the line data and sets at least one of the remaining values of the R value, the G value, and the B value according to the degree of abnormality of the feature vector.

As an embodiment of the present disclosure, the control unit calculates the degree of abnormality of the feature vector using a vector which is different for each type of the object to be detected as the identification vector.

As an embodiment of the present disclosure, the object to be detected includes at least one of a stent, a guide wire, a vessel wall, a calcified lesion, and a plaque.

As an embodiment of the present disclosure, the control unit analyzes the line data to detect a position of a blood cell region that is present in the transmission direction of the ultrasound and calculates a degree of abnormality of a vector, from which an element corresponding to the detected position has been excluded, as the degree of abnormality of the feature vector.

As an embodiment of the present disclosure, the control unit generates, as the detection image, a developed image in which the biological tissue is cut open along a movement direction of the ultrasound transducer.

According to another aspect of the present disclosure, there is provided a diagnosis assistance system including the diagnosis assistance device and a probe including the ultrasound transducer.

According to still another aspect of the present disclosure, there is provided a diagnosis assistance method including: allowing an ultrasound transducer to radially transmit ultrasound while being moved inside a biological tissue; allowing a diagnosis assistance device to generate line data indicating an intensity value of a reflected wave from a reflection object, which is present in a transmission direction of the ultrasound, for each combination of a movement position of the ultrasound transducer and the transmission direction of the ultrasound with reference to an observation result of a cross section of the biological tissue by the ultrasound transducer; and allowing the diagnosis assistance device to generate a detection image which includes pixels corresponding to the generated line data and in which the pixels corresponding to the line data at the same movement position are arranged in one direction, the pixels corresponding to the line data in the same transmission direction are arranged in a direction perpendicular to the one direction, and each pixel value is set according to a degree of abnormality of the generated line data.

According to another aspect, a diagnosis assistance device is connectable to an ultrasound transducer that is positionable inside biological tissue and is axially movable along the biological tissue while radially outwardly transmitting ultrasound. The diagnosis assistance device comprises: a control unit configured to generate line data indicating an intensity value of a reflected wave from a reflection object, which is present in a transmission direction of the ultrasound, for each combination of an axial movement position of the ultrasound transducer and a transmission direction of the ultrasound with reference to an observation result of a cross section of the biological tissue by the ultrasound transducer; and memory connected to the control unit and configured to store the generated line data indicating the intensity value of the reflected wave from the reflection object. The control unit is configured to generate a detection image that includes pixels corresponding to the generated line data, with the pixels corresponding to the line data at a common axial movement position of the ultrasound transducer being arranged in one direction, the pixels corresponding to the line data in a common transmission direction being arranged in a direction perpendicular to the one direction, and each pixel value being set according to a degree of abnormality of the generated line data. The memory is configured to store the detection image.

According to an embodiment of the present disclosure, it is possible to generate an image, in which the state of an object to be detected can be observed, from an observation result of a cross section of a biological tissue by ultrasound.

DETAILED DESCRIPTION

Figure 1:
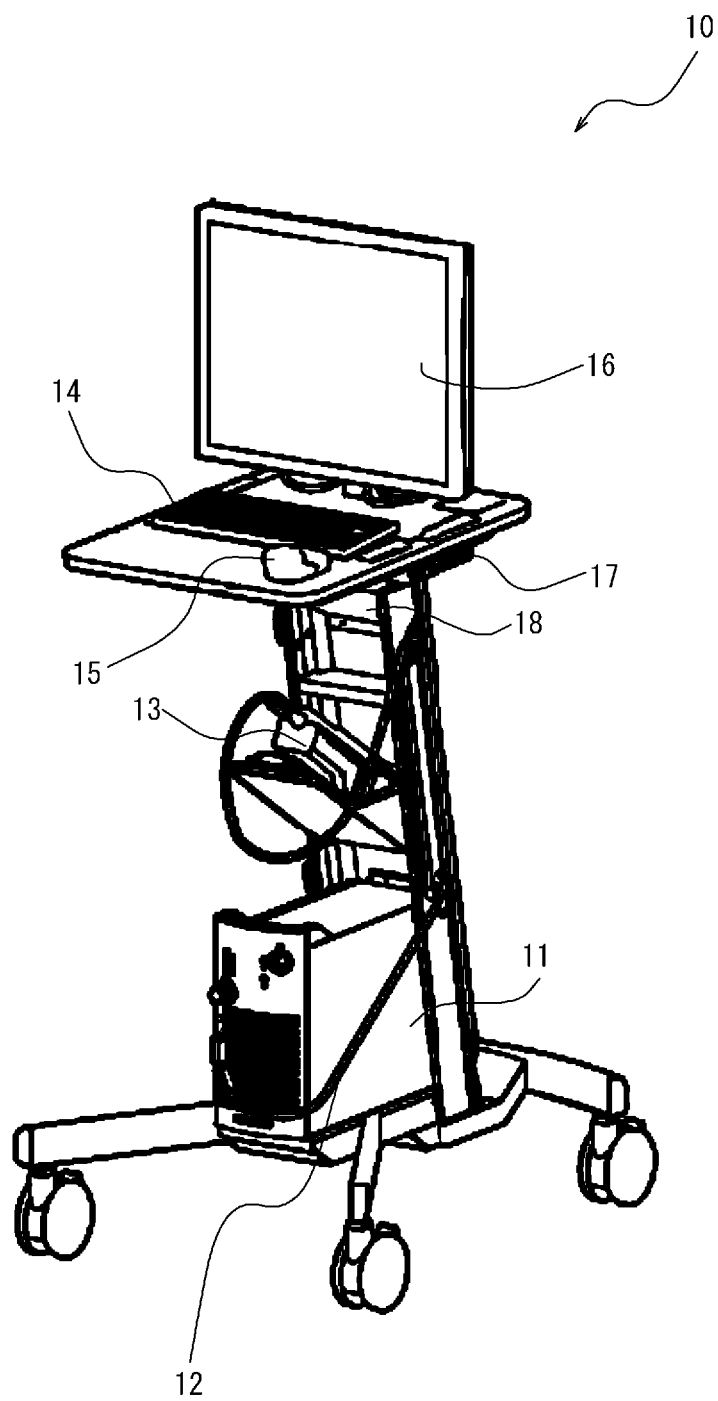
FIG. 1 is a perspective view illustrating a diagnosis assistance system according to an embodiment of the present disclosure.

Hereinafter, an embodiment of the diagnosis assistance device, system and method, representing examples of the new diagnosis assistance device, system and method disclosed here, will be described with reference to the accompanying drawings.

In each of the drawings, the same or equivalent portions/features are denoted by the same reference numerals. In the description of this embodiment, a detailed description of the same or equivalent features/portions is not repeated.

A general outline of this embodiment will be described with reference to FIG. 1, FIG. 2, and FIG. 3.

In this embodiment, an ultrasound transducer 25 radially transmits ultrasound while moving inside a biological tissue (e.g., a vascular lumen or blood vessel lumen). A diagnosis assistance device 11 generates line data $L[z, \theta]$ indicating an intensity value of a reflected wave from a reflection object, which is present in a transmission direction $\theta$ of the ultrasound, for each combination of a movement position z of the ultrasound transducer 25 and the transmission direction $\theta$ of the ultrasound with reference to the observation result of the cross section of the biological tissue by the ultrasound transducer 25. The diagnosis assistance device 11 generates a detection image which includes pixels $P[z, \theta]$ corresponding to the generated line data $L[z, \theta]$ and in which the pixels $P[z, \theta]$ corresponding to the line data $L[z, \theta]$ at the same movement position z are arranged in one direction, the pixels $P[z, \theta]$ corresponding to the line data $L[z, \theta]$ in the same transmission direction $\theta$ are arranged in a direction perpendicular to the one direction, and each pixel value is set according to the degree of abnormality of the generated line data $L[z, \theta]$.

According to this embodiment, it is possible to generate an image in which the state of an object to be detected can be observed from the observation result of the cross section of the biological tissue by the ultrasound. The biological tissue to be observed is a blood vessel in this embodiment, but may be an organ, such as the heart, or other biological tissues. The object to be detected is a stent in this embodiment, but may be a guide wire, a vessel wall, a calcified lesion, a plaque, or other reflection objects. For example, the object to be detected includes at least one of the stent, the guide wire, the vessel wall, the calcified lesion, and the plaque.

In this embodiment, data indicating an intensity value distribution $A[z, \theta]$ of the reflected wave in the transmission direction $\theta$ of the ultrasound is generated as the line data $L[z, \theta]$.

In this embodiment, a cross-sectional image 50 having a brightness value distribution corresponding to the intensity value distribution $A[z, \theta]$ is referred to as the observation result of the cross section of the biological tissue. The cross-sectional image 50 is, specifically, an IVUS two-dimensional image.

In this embodiment, a developed image 60 in which the biological tissue is cut open along the movement direction of the ultrasound transducer 25 is generated as the detection image. The developed image 60 is, specifically, a color map.

In this embodiment, the features of the line data $L[z, \theta]$ are extracted, and the degree of abnormality of a feature vector p indicating the extracted features is calculated. That is, the degree of abnormality of the feature vector p indicating the features of the line data $L[z, \theta]$ is calculated as the degree of abnormality of the line data $L[z, \theta]$. Specifically, the feature vector p is a vector indicating the intensity value distribution $A[z, \theta]$.

In this embodiment, comparison C between the feature vector p and an identification vector q for identifying the object to be detected is performed, and the degree of abnormality of the feature vector p is calculated as the result of the comparison C. Specifically, the identification vector q is a vector indicating an identification pattern of the object to be detected. Specifically, the degree of abnormality of the feature vector p is a similarity between the feature vector p and the identification vector q.

The configuration of a diagnosis assistance system 10 according to this embodiment will be described with reference to FIG. 1.

The diagnosis assistance system 10 includes the diagnosis assistance device 11, a cable 12, a drive unit 13, a keyboard 14, a mouse 15, and a display 16.

The diagnosis assistance device 11 is a dedicated computer that is specialized for diagnostic imaging in this embodiment, but may be a general-purpose computer such as a PC. The "PC" is an abbreviation of personal computer.

The cable 12 is used to connect the diagnosis assistance device 11 and the drive unit 13.

Figure 2:
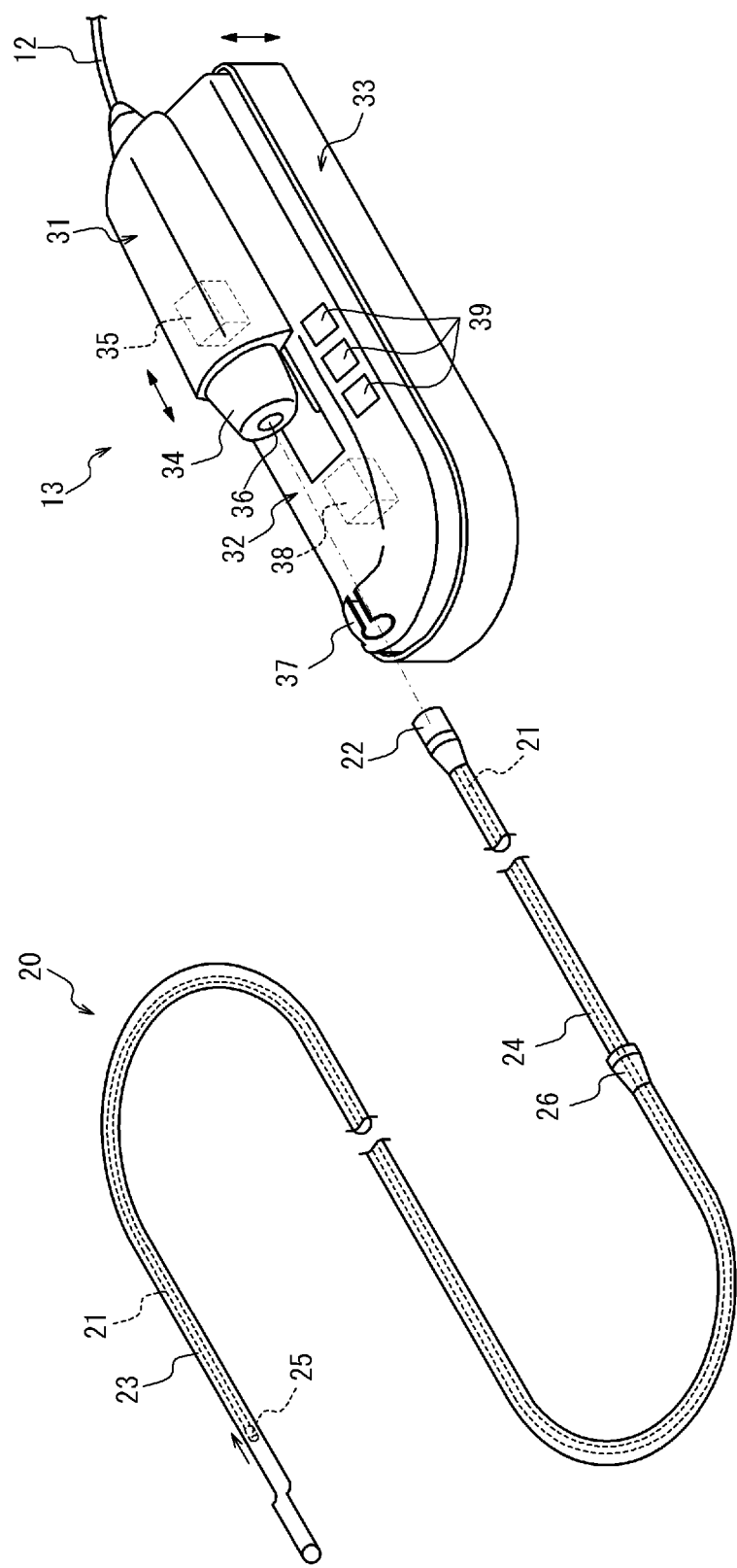
FIG. 2 is a perspective view illustrating a probe and drive unit according to the embodiment of the present disclosure.

The drive unit 13 is a device that is connected to a probe 20 illustrated in FIG. 2 and is used to drive the probe 20. The drive unit 13 is also called as an MDU. The "MDU" is an abbreviation of motor drive unit. The probe 20 is applied to the IVUS. The probe 20 is also called an IVUS catheter or a diagnostic imaging catheter.

The keyboard 14, the mouse 15, and the display 16 are connected to the diagnosis assistance device 11 through any cables or wirelessly. The display 16 is, for example, an LCD, an organic EL display, or an HMD. The "LCD" is an abbreviation of liquid crystal display. The "EL" is an abbreviation of electro luminescence. The "HMD" is an abbreviation of head-mounted display.

The diagnosis assistance system 10 further includes a connection terminal 17 and a cart unit 18 as options.

The connection terminal 17 is used to connect the diagnosis assistance device 11 and an external device. The connection terminal 17 is, for example, a USB terminal. The "USB" is an abbreviation of Universal Serial Bus. The external device is, for example, a recording medium such as a magnetic disk drive, a magneto-optical disk drive, or an optical disk drive.

The cart unit 18 is a cart with casters for movement. The diagnosis assistance device 11, the cable 12, and the drive unit 13 are installed in a cart main body of the cart unit 18. The keyboard 14, the mouse 15, and the display 16 are installed on a table at the top of the cart unit 18.

The configuration of the probe 20 and the drive unit 13 according to this embodiment will be described with reference to FIG. 2.

The probe 20 includes a drive shaft 21, a hub 22, a sheath 23, an outer tube 24, the ultrasound transducer 25, and a relay connector 26.

The drive shaft 21 passes through the sheath 23 inserted into the body cavity of a living body and the outer tube 24 connected to a base end of the sheath 23 and extends to the inside of the hub 22 provided at a base end of the probe 20. The drive shaft 21 has the ultrasound transducer 25, which transmits and receives signals, at the distal end and is rotatably provided in the sheath 23 and the outer tube 24. The relay connector 26 connects the sheath 23 and the outer tube 24.

The hub 22, the drive shaft 21, and the ultrasound transducer 25 are connected to each other so as to be integrally moved forward and backward in an axial direction. Therefore, for example, when an operation of pushing the hub 22 to the distal end or in the distal direction is performed, the drive shaft 21 and the ultrasound transducer 25 are moved to the distal end or in the distal direction in the sheath 23. For example, when an operation of pulling the hub 22 to the base end or in the rearward/proximal direction is performed, the drive shaft 21 and the ultrasound transducer 25 are moved to the base end or in the proximal/rearward direction in the sheath 23 as represented by an arrow.

The drive unit 13 includes a scanner unit 31, a slide unit 32, and a bottom cover 33.

The scanner unit 31 is connected to the diagnosis assistance device 11 through the cable 12. The scanner unit 31 includes a probe connection portion 34 connected to the probe 20 and a scanner motor 35 which is a driving source for rotating the drive shaft 21.

The probe connection portion 34 is removably connected to the probe 20 by virtue of the base end of the probe 20 being inserted into or positioned in an insertion hole 36 of the probe connection portion 34. In the hub 22, the base end of the drive shaft 21 is rotatably supported, and the rotational force of the scanner motor 35 is transmitted to the drive shaft 21. In addition, signals are transmitted and received between the drive shaft 21 and the diagnosis assistance device 11 through the cable 12. The diagnosis assistance device 11 performs the generation of a tomographic image of a biological lumen and image processing on the basis of the signals transmitted from the drive shaft 21.

The scanner unit 31 is mounted on the slide unit 32 so as to be movable forward and backward, and the slide unit 32 is mechanically and electrically connected to the scanner unit 31. The slide unit 32 includes a probe clamp portion 37, a slide motor 38, and a switch group 39.

The probe clamp portion 37 is provided closer to the distal end than the probe connection portion 34 so as to be disposed coaxially with the probe connection portion 34 and supports the probe 20 connected to the probe connection portion 34.

The slide motor 38 is a drive source that generates a driving force in the axial direction. The scanner unit 31 is moved forward and backward by the driving of the slide motor 38, and the drive shaft 21 is moved forward and backward in the axial direction with the movement of the scanner unit 31. The slide motor 38 is, for example, a servo-motor.

The switch group 39 includes, for example, a forward switch and a pullback switch which are pressed at the time of the operation of moving the scanner unit 31 forward and backward and a scan switch that is pressed when imaging is started and ended. The present disclosure is not limited to this example, and various switches are included in the switch group 39 as needed.

When the forward switch is pressed, the slide motor 38 is rotated forward, and the scanner unit 31 is moved forward. On the other hand, when the pull-back switch is pressed, the slide motor 38 is rotated backward, and the scanner unit 31 is moved backward.

When the scan switch is pressed, imaging is started, and the scanner motor 35 is driven. In addition, the slide motor 38 is driven to move the scanner unit 31 backward. A user, such as an operator, connects the probe 20 to the scanner unit 31 in advance such that the drive shaft 21 is moved to the base end in the axial direction while being rotated with the start of imaging. The scanner motor 35 and the slide motor 38 are stopped when the scan switch is pressed again, and the imaging ends.

The bottom cover 33 covers a bottom surface of the slide unit 32 and the entire periphery of a side surface on the bottom surface side and is provided so as to be close to and separated from the bottom surface of the slide unit 32.

Figure 3:
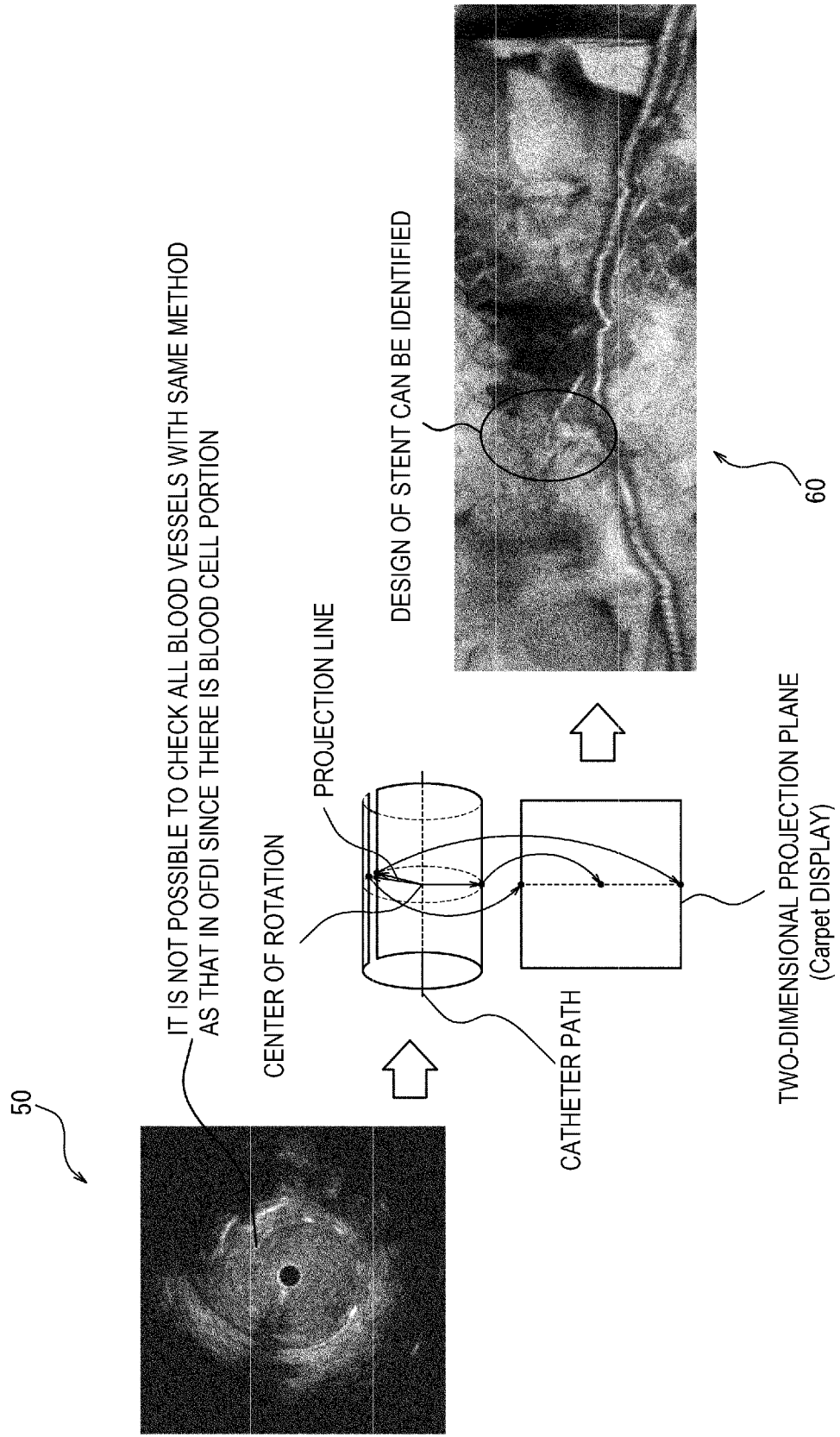
FIG. 3 is a diagram illustrating an example in which a detection image is generated from a cross-sectional image of a biological tissue by a diagnosis assistance device according to the embodiment of the present disclosure.

As illustrated in FIG. 3, in the IVUS cross-sectional image 50, since there is a blood cell portion, it is not possible to check the entire blood vessel using the same method as that in the OFDI. Therefore, in this embodiment, the diagnosis assistance device 11 reconstructs the detection image which is the blood vessel image, using the line data $L[z, \theta]$ that is obtained by moving an imaging core, which transmits an ultrasound signal toward the blood vessel and detects a reflected signal, in a catheter while rotating the imaging core and extends radially from the center of rotation of the imaging core. The imaging core is composed of at least the drive shaft 21 and the ultrasound transducer 25.

Specifically, the diagnosis assistance device 11 generates a reception vector including a value indicating the intensity of the reflected signal and a depth component with reference to the line data $L[z, \theta]$ obtained by the rotation operation of the imaging core. The "depth" is a distance to the reflection object in the transmission direction $\theta$ of the ultrasound signal. The diagnosis assistance device 11 calculates the similarity between the generated reception vector and a detection vector having a characteristic that makes it easy to discriminate the pattern of the reflected waves obtained in a case in which the stent is present in the transmission direction $\theta$ of the ultrasound signal. The diagnosis assistance device 11 classifies data which has been three-dimensionally collected, using the movement position z of the ultrasound transducer 25, the transmission direction $\theta$ of the ultrasound signal, and the similarity as parameters, and displays the classification result. The reception vector corresponds to the feature vector p. The detection vector corresponds to the identification vector q. The similarity corresponds to the degree of abnormality of the feature vector p. The reception vector may include the frequency of occurrence of signal intensity as a component or may include both the depth and the frequency of occurrence as components.

Specifically, the diagnosis assistance device 11 maps each reception vector to a polar coordinate space, performs projection in the radial direction of the blood vessel, and assigns a color on a projection plane using the similarity to generate the developed image 60 in which the blood vessel is cut open in a long axis direction. The color corresponds to the pixel value of a pixel $P[z, \theta]$.

According to this embodiment, the design of the stent can be identified by the color in the developed image 60. In particular, the developed image 60 is useful for evaluating the narrowing and dissociation of the side branch ostium of the bifurcation and the deformation of the stent after side branch dilation.

Figure 4:
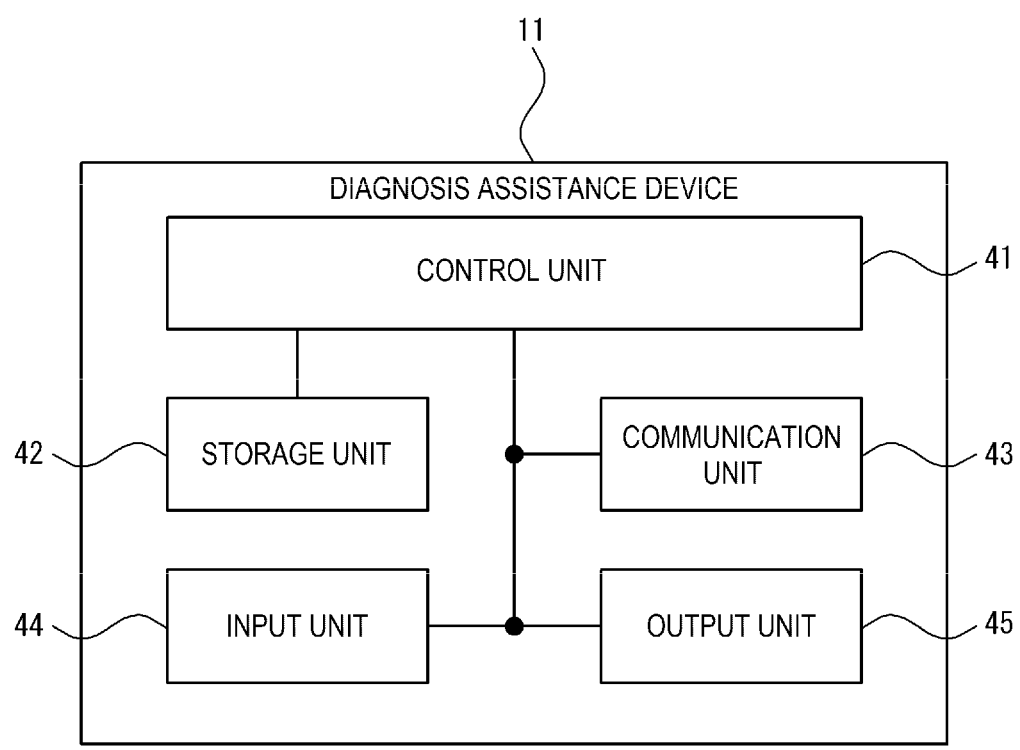
FIG. 4 is a block diagram illustrating a configuration of the diagnosis assistance device according to the embodiment of the present disclosure.

The configuration of the diagnosis assistance device 11 according to this embodiment will be described with reference to FIG. 4.

The diagnosis assistance device 11 includes components such as a control unit 41, a storage unit 42, a communication unit 43, an input unit 44, and an output unit 45.

The control unit 41 is one or more processors. The processor is a general-purpose processor, such as a CPU or a GPU, or a dedicated processor specialized for a specific process. The "CPU" is an abbreviation of central processing unit. The "GPU" is an abbreviation of graphics processing unit. The control unit 41 may include one or more dedicated circuits. Alternatively, in the control unit 41, one or more processors may be replaced with one or more dedicated circuits. The dedicated circuit is, for example, an FPGA or an ASIC. The "FPGA" is an abbreviation of field-programmable gate array. The "ASIC" is an abbreviation of application specific integrated circuit. The control unit 41 performs information processing related to the operation of the diagnosis assistance device 11 while controlling each unit of the diagnosis assistance system 10 including the diagnosis assistance device 11.

The storage unit 42 is one or more semiconductor memories, one or more magnetic memories, one or more optical memories, or a combination of at least two of them. The semiconductor memory is, for example, a RAM or a ROM. The "RAM" is an abbreviation of random access memory. The "ROM" is an abbreviation of read only memory. The RAM is, for example, an SRAM or a DRAM. The "SRAM" is an abbreviation of static random access memory. The "DRAM" is an abbreviation of dynamic random access memory. The ROM is, for example, an EEPROM. The "EEPROM" is an abbreviation of electrically erasable programmable read only memory. The storage unit 42 functions as, for example, a main storage device, an auxiliary storage device, or a cache memory. The storage unit 42 stores information used for the operation of the diagnosis assistance device 11 and information obtained by the operation of the diagnosis assistance device 11.

The communication unit 43 is one or more communication interfaces. The communication interface is a wired LAN interface, a wireless LAN interface, or a diagnostic imaging interface that receives IVUS signals and performs A/D conversion on the IVUS signals. The "LAN" is an abbreviation of local area network. The "A/D" is an abbreviation of analog to digital. The communication unit 43 receives the information used for the operation of the diagnosis assistance device 11 and transmits the information obtained by the operation of the diagnosis assistance device 11. In this embodiment, the drive unit 13 is connected to the diagnostic imaging interface included in the communication unit 43.

The input unit 44 is one or more input interfaces. The input interface is, for example, a USB interface or an HDMI (registered trademark) interface. The "HDMI (registered trademark)" is an abbreviation of High-Definition Multimedia Interface. The input unit 44 receives an operation of inputting the information used for the operation of the diagnosis assistance device 11. In this embodiment, the keyboard 14 and the mouse 15 are connected to the USB interfaces included in the input unit 44. However, the keyboard 14 and the mouse 15 may be connected to the wireless LAN interfaces included in the communication unit 43.

The output unit 45 is one or more output interfaces. The output interface is, for example, a USB interface or an HDMI (registered trademark) interface. The output unit 45 outputs the information obtained by the operation of the diagnosis assistance device 11. In this embodiment, the display 16 is connected to the HDMI (registered trademark) interface included in the output unit 45.

The processor included in the control unit 41 executes a diagnosis assistance program according to this embodiment to implement the functions of the diagnosis assistance device 11. That is, the functions of the diagnosis assistance device 11 are implemented by software. The diagnosis assistance program is a program for causing a computer to perform processes in steps included in the operation of the diagnosis assistance device 11 so as to implement functions corresponding to the processes in the steps. That is, the diagnosis assistance program is a program for causing the computer to function as the diagnosis assistance device 11.

The program can be recorded on a computer-readable recording medium. The computer-readable recording medium is, for example, a magnetic recording medium, an optical disk, a magneto-optical recording medium, or a semiconductor memory. The program is distributed, for example, by selling, transferring, or renting a portable recording medium such as a DVD or a CD-ROM having the program recorded thereon. The "DVD" is an abbreviation of digital versatile disc. The "CD-ROM" is an abbreviation of compact disc read only memory. The program may be distributed by storing the program in a storage of a server and transmitting the program from the server to another computer through the network. The program may be provided as a program product.

For example, the computer temporarily stores the program recorded on the portable recording medium or the program transmitted from the server in the main storage device. Then, in the computer, the processor reads the program stored in the main storage device and performs a process according to the read program. The computer may read the program directly from the portable recording medium and perform the process according to the program. The computer may sequentially perform the process according to the received program each time the program is transmitted from the server to the computer. The process may be performed by a so-called ASP-type service that implements functions only by an execution instruction and the acquisition of results without transmitting the program from the server to the computer. The "ASP" is an abbreviation of application service provider. The program includes information that is used for the processes of an electronic computer and is equivalent to the program. For example, data that is not a direct command to the computer but has the property of defining the processes of the computer corresponds to the "information equivalent to the program".

Some or all of the functions of the diagnosis assistance device 11 may be implemented by the dedicated circuit included in the control unit 41. That is, some or all of the functions of the diagnosis assistance device 11 may be implemented by hardware.

The operation of the diagnosis assistance system 10 according to this embodiment will be described with reference to FIG. 5. The operation of the diagnosis assistance system 10 corresponds to a diagnosis assistance method according to this embodiment.

Figure 5:
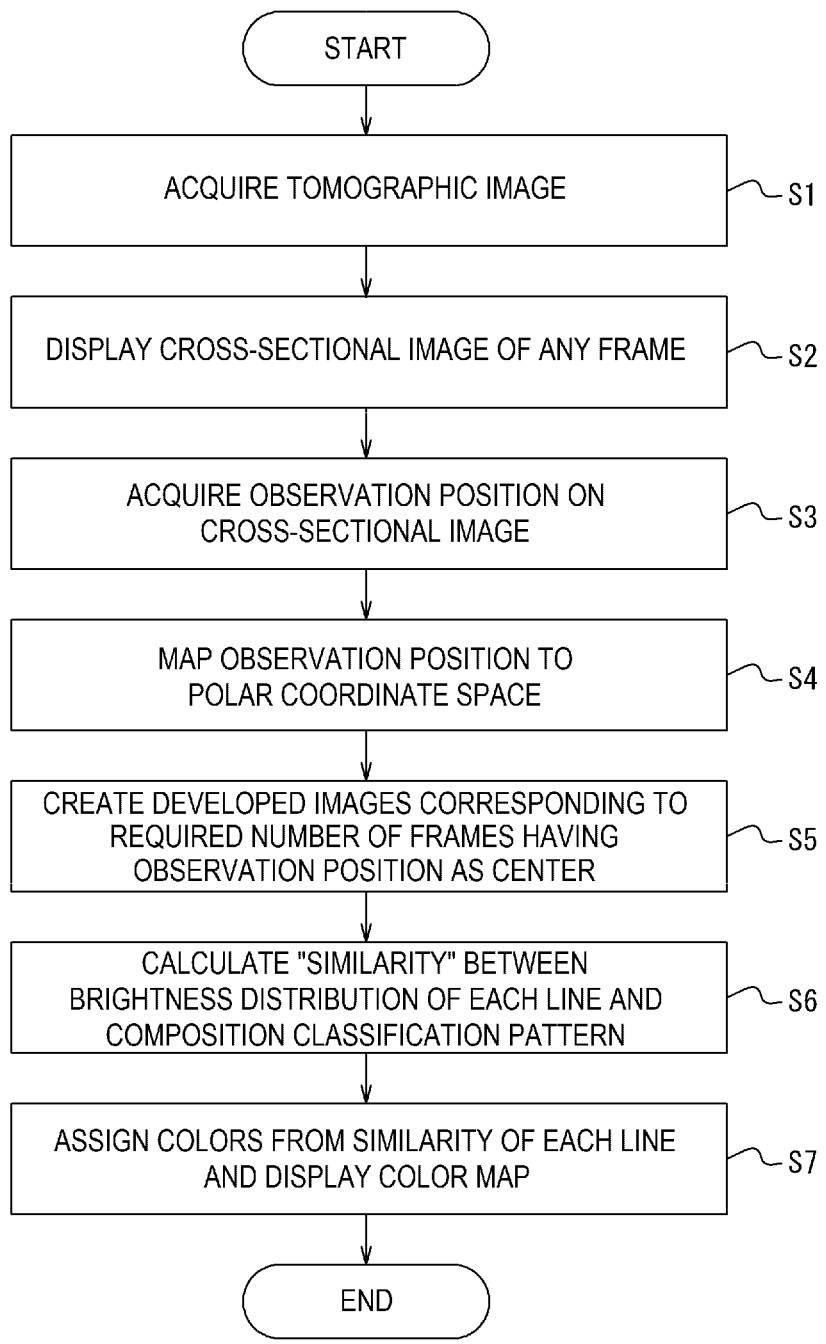
FIG. 5 is a flowchart illustrating an operation of the diagnosis assistance system according to the embodiment of the present disclosure.

Before the flow or operation illustrated in FIG. 5 is started, the user primes the probe 20. Then, the probe 20 is fitted to the probe connection portion 34 and the probe clamp portion 37 of the drive unit 13 and is connected and fixed to the drive unit 13. Then, the probe 20 is inserted into a target part in the blood vessel.

In Step S1, a so-called pullback operation (tomographic image acquisition) is performed by pressing the scan switch included in the switch group 39 and further pressing the pullback switch included in the switch group 39. The probe 20 transmits ultrasound inside the blood vessel using the ultrasound transducer 25 that is moved backward in the axial direction by the pullback operation. The ultrasound transducer 25 radially transmits the ultrasound while being moved inside the blood vessel. The ultrasound transducer 25 receives a reflected wave of the transmitted ultrasound. The probe 20 inputs a signal of the reflected wave received by the ultrasound transducer 25 to the control unit 41 of the diagnosis assistance device 11. The control unit 41 processes the input signal to sequentially generate the cross-sectional image 50 of the blood vessel and acquires tomographic images including a plurality of cross-sectional images 50.

Figure 6:
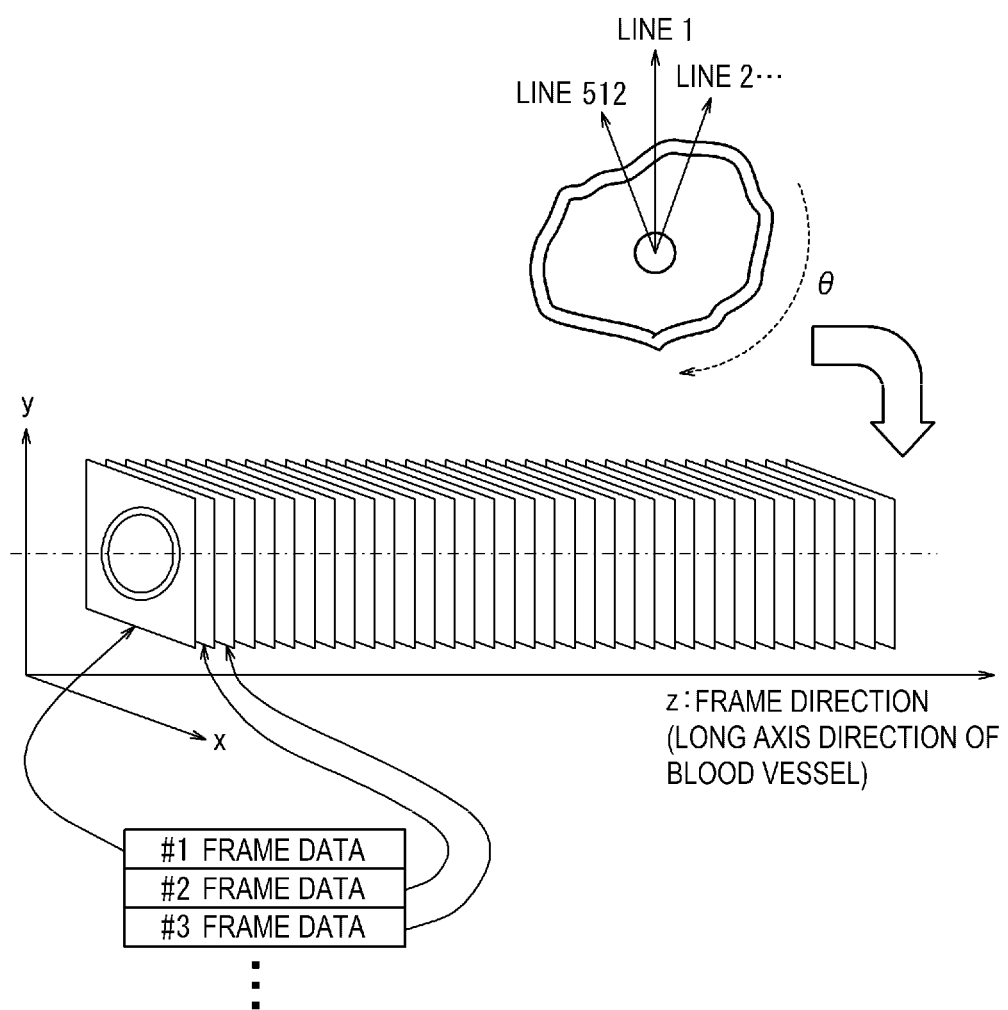
FIG. 6 is a diagram illustrating an example in which a tomographic image is acquired by the diagnosis assistance device according to the embodiment of the present disclosure.

Specifically, as illustrated in FIG. 6, the probe 20 transmits the ultrasound in 512 directions from the center of rotation to the outside using the ultrasound transducer 25 while rotating the ultrasound transducer 25 in a θ direction and moving the ultrasound transducer 25 in the z direction inside the blood vessel. The probe 20 receives the reflected waves from reflection objects that are present in each of the 512 directions inside the blood vessel using the ultrasound transducer 25. The probe 20 transmits a signal of the received reflected waves to the diagnosis assistance device 11 through the drive unit 13 and the cable 12. The communication unit 43 of the diagnosis assistance device 11 receives the signal transmitted from the probe 20. The communication unit 43 performs A/D conversion on the received signal. The communication unit 43 inputs the signal subjected to the A/D conversion to the control unit 41. The control unit 41 processes the input signal to sequentially generate frame data on the IVUS cross-sectional image 50, thereby generating an IVUS tomographic image. The control unit 41 stores the generated tomographic image in the storage unit 42.

As a modification example of this embodiment, an ultrasound transducer that transmits ultrasound in a plurality of directions without being rotated may be used instead of the ultrasound transducer 25 that transmits the ultrasound in a plurality of directions while being rotated in the θ direction.

As a modification example of this embodiment, instead of the configuration in which the diagnosis assistance device 11 generates the tomographic image, another device may generate the tomographic image, and the diagnosis assistance device 11 may acquire the tomographic image from another device. That is, instead of the configuration in which the control unit 41 of the diagnosis assistance device 11 processes the IVUS signal to generate the cross-sectional image 50 of the blood vessel, another device may process the IVUS signal to generate the cross-sectional image 50 of the blood vessel and input the generated cross-sectional image 50 to the control unit 41.

In Step S2, the control unit 41 of the diagnosis assistance device 11 performs control to display any cross-sectional image 50 included in the tomographic images.

Specifically, the control unit 41 displays the cross-sectional image 50 of any frame data included in the tomographic images stored in the storage unit 42 on the display 16 through the output unit 45.

Figure 7:
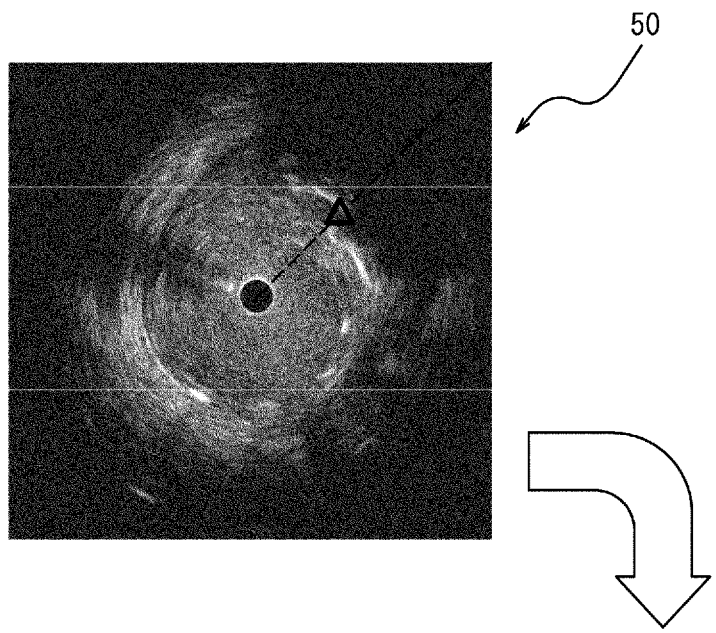
FIG. 7 is a diagram illustrating an example in which the cross-sectional image of the biological tissue is converted into a developed image by the diagnosis assistance device according to the embodiment of the present disclosure.
Figure 7:
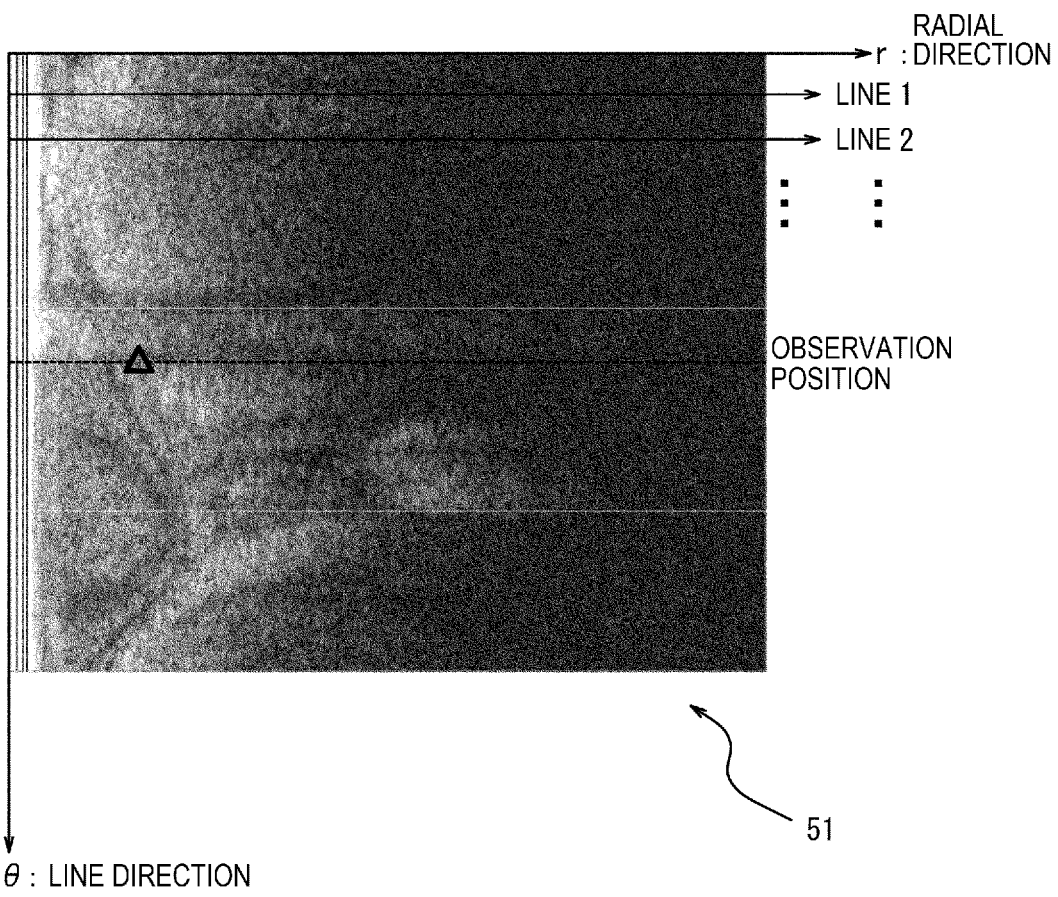

In Step S3, the control unit 41 of the diagnosis assistance device 11 acquires an observation position on the cross-sectional image 50 as illustrated in FIG. 7.

In Step S4, the control unit 41 of the diagnosis assistance device 11 maps the observation position to a polar coordinate space 51 as illustrated in FIG. 7.

In Step S5, the control unit 41 of the diagnosis assistance device 11 creates the developed images 60 corresponding to the required number of frames having the observation position as the center.

Specifically, the control unit 41 generates the line data L[z, θ] for each combination of the movement position z of the ultrasound transducer 25 and the transmission direction θ of the ultrasound, with reference to the observation result of the cross section of the blood vessel by the ultrasound transducer 25. The line data L[z, θ] is data indicating the intensity value distribution A[z, θ] of the reflected waves from the reflection object that is present in the transmission direction θ of the ultrasound. The control unit 41 stores the generated line data L[z, θ] in the storage unit 42. The control unit 41 generates the developed image 60 that includes the pixels P[z, θ] corresponding to the line data L[z, θ] stored in the storage unit 42. The developed image 60 is an image in which the pixels P[z, θ] corresponding to the line data L[z, θ] at the same movement position z are arranged in the θ direction which is one direction, the pixels P[z, θ] corresponding to the line data L[z, θ] in the same transmission direction θ are arranged in the z direction which is a direction perpendicular to the θ direction. The developed image 60 is an image in which the blood vessel is cut open along the movement direction of the ultrasound transducer 25. The control unit 41 stores the generated developed image 60 in the storage unit 42.

For example, the control unit 41 refers to the cross-sectional image 50 of "#1 frame data" illustrated in FIG. 6 as the observation result of the cross section of the blood vessel by the ultrasound transducer 25 at movement position 1. The cross-sectional image 50 of the "#1 frame data" is a two-dimensional image having brightness value distributions corresponding to intensity value distributions A[1, 1] to A[1, 512]. The control unit 41 analyzes the brightness value distribution of "line 1" illustrated in FIGS. 6 and 7 in the cross-sectional image 50 of the "#1 frame data" to generate line data L[1, 1]. The line data L[1, 1] is data indicating the intensity value distribution A[1, 1] of the reflected waves from a reflection object that is present in ultrasound transmission direction 1. In addition, the control unit 41 analyzes the brightness value distribution of "line 2" illustrated in FIGS. 6 and 7 in the cross-sectional image 50 of the "#1 frame data" to generate line data L[1, 2]. The line data L[1, 2] is data indicating the intensity value distribution A[1, 2] of the reflected waves from a reflection object that is present in ultrasound transmission direction 2. Similarly, the control unit 41 analyzes the brightness value distributions of "line 3" to "line 512" in the cross-sectional image 50 of the "#1 frame data" to generate line data L[1, 3] to line data L[1, 512], respectively.

The control unit 41 refers to the cross-sectional image 50 of "#2 frame data" illustrated in FIG. 6 as the observation result of the cross section of the blood vessel by the ultrasound transducer 25 at movement position 2. The cross-sectional image 50 of the "#2 frame data" is a two-dimensional image having brightness value distributions corresponding to intensity value distributions A[2, 1] to A[2, 512]. The control unit 41 analyzes the brightness value distribution of each line in the cross-sectional image 50 of the "#2 frame data" to generate line data L[2, 1] to line data L[2, 512], as in the case of the cross-sectional image 50 of the "#1 frame data".

The control unit 41 generates line data L[z, θ] other than the line data L[1, 1] to the line data L[1, 512] and the line data L[2, 1] to the line data L[2, 512] with reference to the cross-sectional images 50 of "#3 frame data" and the subsequent frame data as in the case of the cross-sectional images 50 of the "#1 frame data" and the "#2 frame data".

In the developed image 60 generated by the control unit 41, the pixels P[1, 1] to P[1, 512] respectively corresponding to the line data L[1, 1] to the line data L[1, 512] at the movement position 1 are arranged in a column. The pixels P[2,1] to P[2, 512] respectively corresponding to the line data L[2, 1] to the line data L[2, 512] at the movement position 2 are arranged in the next column. Similarly, the pixels P[z, θ] corresponding to the line data L[z, θ] at movement position 3 and the subsequent movement positions are sequentially arranged in the next or subsequent columns.

As a modification example of this embodiment, the control unit 41 may convert the intensity value distribution A[z, θ] into a distribution from the center of gravity of the cross section observed by the ultrasound transducer 25 and generate data indicating the converted distribution as the line data L[z, θ]. The "cross section observed by the ultrasound transducer 25" is the cross section of the biological tissue. However, it is assumed that the stent is also regarded as a portion of the biological tissue at the position where the stent is placed or located. Specifically, the control unit 41 may calculate the brightness value distribution from the center of gravity of the cross section of the blood vessel with reference to the cross-sectional image 50 and generate data indicating the calculated brightness value distribution as the line data L[z, θ]. That is, the control unit 41 may analyze the IVUS image to detect a cross-sectional component of the blood vessel and reconstruct, as the line data L[z, θ], data indicating the intensity value distribution obtained by rθ reverse conversion from the position of the center of gravity of the blood vessel.

According to this modification example, the starting point of the intensity value distribution A[z, θ] indicated by the line data L[z, θ] at each movement position z is aligned with the position of the center of gravity of the cross section from the movement position z of the ultrasound transducer 25. Therefore, it is possible to more accurately express the shape of the object to be detected in the finally obtained detection image.

Figure 8:
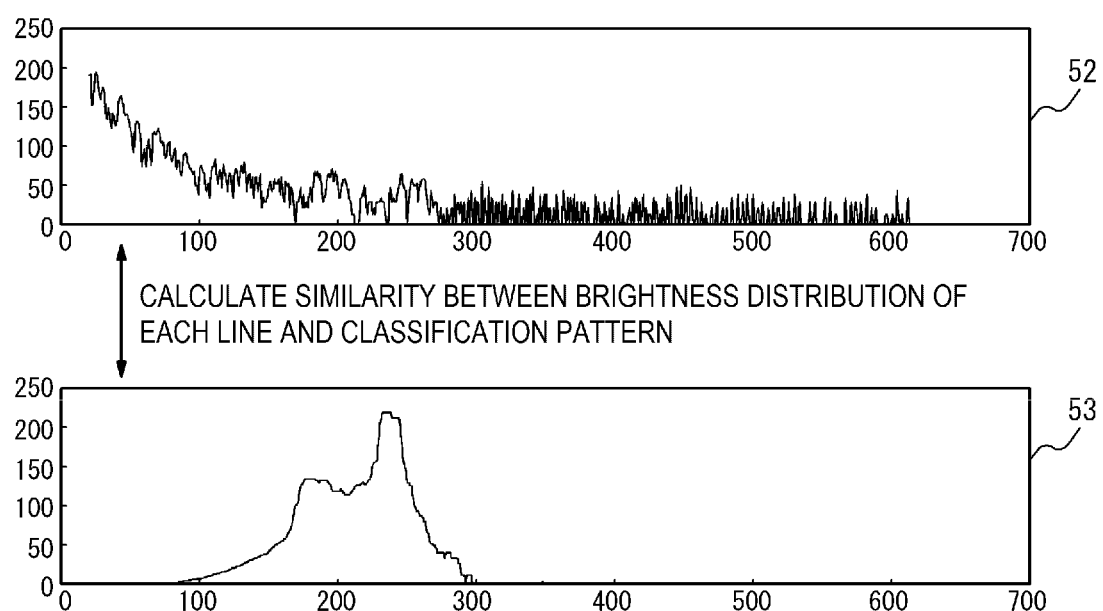
FIG. 8 is a diagram illustrating an example in which a brightness distribution of lines and a classification pattern are compared by the diagnosis assistance device according to the embodiment of the present disclosure.

In Step S6, the control unit 41 of the diagnosis assistance device 11 calculates the similarity between a brightness distribution 52 of each line and a classification pattern 53 which is a pattern of brightness with respect to the depth as illustrated in FIG. 8.

Specifically, the control unit 41 extracts the features of the line data L[z, θ] stored in the storage unit 42 and stores the feature vector p indicating the extracted features in the storage unit 42. That is, the control unit 41 stores the feature vector p indicating the intensity value distribution A[z, θ] indicated by the line data L[z, θ] in the storage unit 42. The control unit 41 calculates the similarity between the feature vector p stored in the storage unit 42 and the identification vector q, which has been stored in the storage unit 42 in advance and is used to identify the stent present in the transmission direction θ of the ultrasound, to perform the comparison C between the feature vector p and the identification vector q. The control unit 41 stores the similarity as the result of the comparison C in the storage unit 42. That is, the control unit 41 calculates the degree of abnormality of the feature vector p as the result of the comparison C and stores the calculated degree of abnormality in the storage unit 42.

For example, the control unit 41 calculates the similarity between the brightness distribution 52 corresponding to the intensity value distribution A[1, 1] indicated by the line data L[1, 1] and the classification pattern 53 of the stent which has been defined in advance. In addition, the control unit 41 calculates the similarity between the brightness distribution 52 corresponding to the intensity value distribution A[1, 2] indicated by the line data L[1, 2] and the classification pattern 53 of the stent. Similarly, the control unit 41 calculates the similarities between the brightness distributions 52 corresponding to the intensity value distributions A[z, θ] indicated by other line data L[z, θ] and the classification pattern 53 of the stent.

Any method may be used to calculate the similarity. However, in this embodiment, an algorithm of cluster analysis or a nearest neighbor classification method is used. An example of this algorithm is a k-means method. The cluster analysis is a method that classifies an object to be classified into the closest class on the basis of a distance in a feature space. The "distance" is an index indicating the similarity and is, for example, a cosine similarity, a Euclidean distance, a standardized Euclidean distance, an average Euclidean distance, a Mahalanobis distance, a Pearson's correlation coefficient, a Jaccard coefficient, or a deviation pattern similarity. The cosine similarity is an index indicating the closeness of the angle between vectors. The Euclidean distance is an index indicating the closeness of the distance between vectors. The Mahalanobis distance is a distance normalized by variance. In the cluster analysis, classification is performed so as to minimize the distance between an input pattern and a representative pattern of each class. However, in this embodiment, the distance is used to create the color map.

An example of an expression for calculating the cosine similarity as the similarity between the feature vector p and the identification vector q is given below.

$$\cos(\vec{p}, \vec{q}) = \frac{p_1 q_1 + p_2 q_2 \cdots p_n q_n}{\sqrt{p_1^2 + p_2^2 + \cdots p_n^2}\sqrt{q_1^2 + q_2^2 + \cdots q_n^2}} = \frac{\sum_{i=0}^{n} p_n q_n}{\sqrt{\sum_{i=0}^{n} p^2}\sqrt{\sum_{i=0}^{n} q^2}} \quad [\text{Math 1}]$$

As a modification example of this embodiment, a different classification pattern 53 may be used for each type of object to be detected such as a stent, a guide wire, a vessel wall, a calcified lesion, and a plaque. That is, the control unit 41 may use a vector, which is different for each type of object to be detected, as the identification vector q to calculate the degree of abnormality of the feature vector p.

According to this modification example, since the similarity changes depending on the type of the object to be detected, each type of object to be detected can be displayed in different colors in the finally obtained detection image.

As a modification example of this embodiment, the control unit 41 may analyze the line data L[z, θ] to detect the position of a blood cell region that is present in the transmission direction θ of the ultrasound, and calculate, as the degree of abnormality of the feature vector p, the degree of abnormality of a vector from which an element corresponding to the detected position has been excluded. For example, the control unit 41 may analyze the line data L[z, θ] to detect a region in which a change in the intensity value from neighboring data is larger than a predetermined threshold value and may suppress data that is located inside the region or exclude the data from the object to be calculated. Alternatively, the control unit 41 may analyze the line data L[z, θ] to detect a region in which the intensity value is larger than a predetermined threshold value and may suppress data that is located inside the region or exclude the data from the object to be calculated.

According to this modification example, it is possible to more reliably suppress the influence of blood cell noise.

Figure 9:
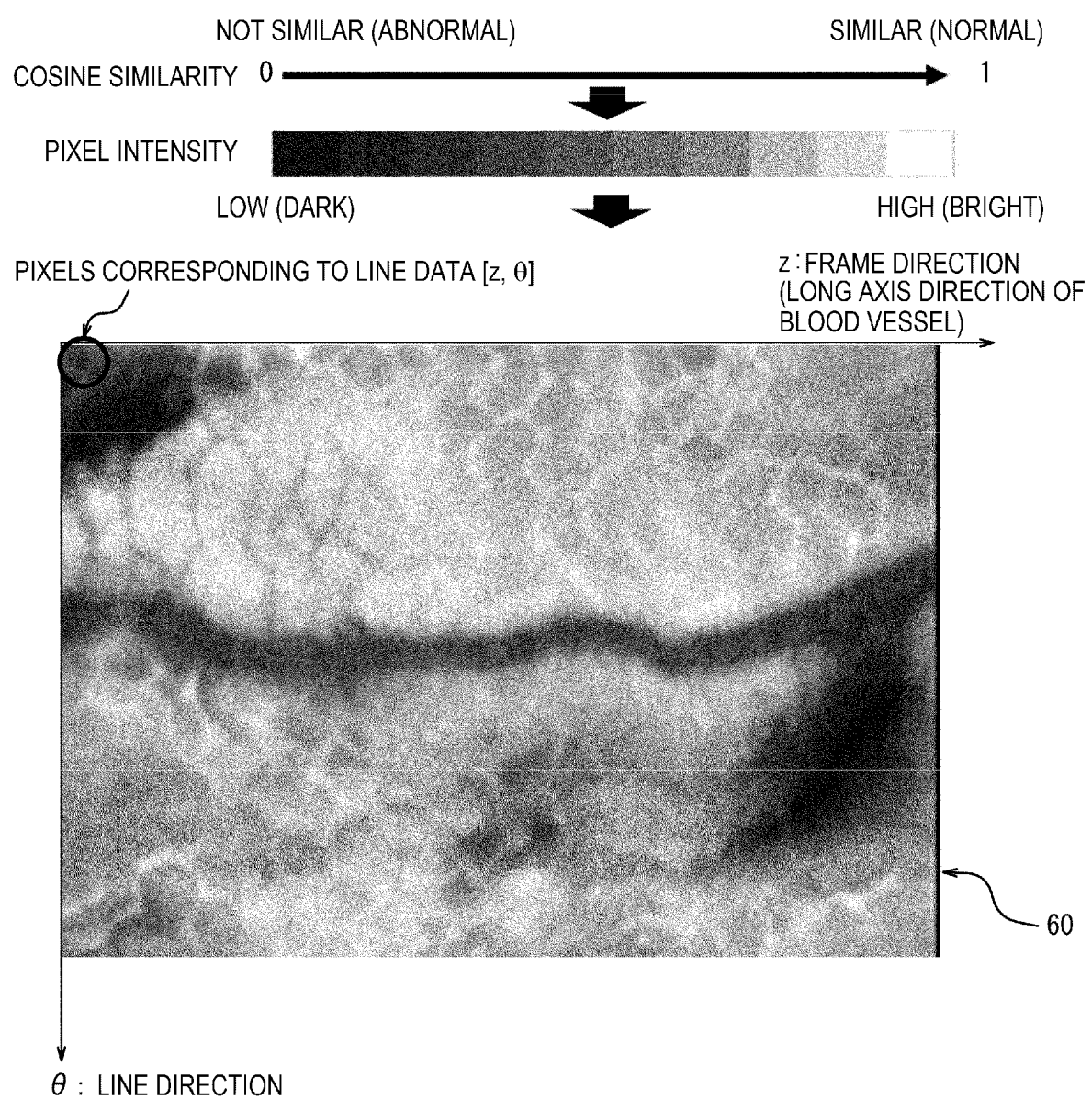
FIG. 9 is a diagram illustrating an example in which the detection image is generated by the diagnosis assistance device according to the embodiment of the present disclosure.

In Step S7, the control unit 41 of the diagnosis assistance device 11 performs control to assign a color to the developed image 60 on the basis of the similarity of each line and to display the developed image 60 as a color map as illustrated in FIG. 9.

Specifically, the control unit 41 sets each pixel value of the developed image 60 stored in the storage unit 42 on the basis of the result of the comparison C stored in the storage unit 42. That is, the control unit 41 sets each pixel value of the developed image 60 to a value corresponding to the similarity between the feature vector p and the identification vector q. As a result, a detection image which includes the pixels P[z, θ] corresponding to the line data L[z, θ] and in which the pixels P[z, θ] corresponding to the line data L[z, θ] at the same movement position z are arranged in the θ direction, the pixels P[z, θ] corresponding to the line data L[z, θ] in the same transmission direction θ are arranged in the z direction, and each pixel value is set on the basis of the result of the comparison C is obtained. Each pixel value is a color in this embodiment and is, specifically, an RGB value. However, each pixel value may be brightness, a combination of a color and brightness, or other pixel values. The control unit 41 displays the obtained detection image on the display 16 through the output unit 45. In the example illustrated in FIG. 9, the control unit 41 sets each pixel value of the developed image 60 such that, as the cosine similarity between the feature vector p and the identification vector q which corresponds to the degree of abnormality of the feature vector p becomes higher, pixel intensity corresponding to the pixel value of the corresponding pixel becomes higher.

As a modification example of this embodiment, the control unit 41 may calculate the degree of abnormality of the feature vector p using at least two different vectors as the identification vector q. When the RGB value of each pixel P[z, θ] is set as each pixel value of the detection image, the control unit may set at least two of the R value, the G value, and the B value according to the degree of abnormality calculated using different vectors. Alternatively, when the RGB value of each pixel P[z, θ] is set as each pixel value of the detection image, the control unit 41 may set one or two of the R value, the G value, and the B value according to the statistics of the line data L[z, θ] and set at least one of the remaining values of the R value, G value, and B value according to the degree of abnormality of the feature vector p. For example, the control unit 41 may set the G value according to the cosine similarity corresponding to the degree of abnormality of the feature vector p, set the R value according to the standard deviation of a brightness value equal to or greater than a predetermined threshold value which corresponds to a statistic of the line data L[z, θ], and set the B value according to the proportion of the bright value equal to or greater than the predetermined threshold value to the line which corresponds to another statistic of the line data L[z, θ].

According to this modification example, for example, even when the cosine similarity between the brightness distribution 52 of the line in which the stent is actually present and the classification pattern 53 for detecting the stent is small, it is possible to set at least one of the R value, the G value, and the B value to a value corresponding to the stent, using the statistics of the line. Therefore, it is possible to accurately display the object to be detected in a different color in the finally obtained detection image.

As a modification example of this embodiment, the control unit 41 may receive an operation of selecting the position that the user wants to display in the detection image through the input unit 44. In this case, the control unit 41 displays the detection image having the selected position as the center on the display 16 through the output unit 45. Alternatively, the control unit 41 may receive an operation of selecting a display range in the z direction through the input unit 44. In this case, the control unit 41 generates a detection image in the selected display range and displays the generated detection image on the display 16 through the output unit 45. The display range is selected by a combination of the position in the z direction and the size in the z direction based on the position.

As described above, in this embodiment, the control unit 41 of the diagnosis assistance device 11 generates the line data L[z, θ] indicating the intensity value of the reflected wave from the reflection object, which is present in the transmission direction θ of the ultrasound, for each combination of the movement position z of the ultrasound transducer 25 that radially transmits the ultrasound while being moved in the biological tissue and the transmission direction θ of the ultrasound with reference to the observation result of the cross section of the biological tissue by the ultrasound transducer 25. The control unit 41 generates the detection image which includes the pixels P[z, θ] corresponding to the generated line data L[z, θ] and in which the pixels P[z, θ] corresponding to the line data L[z, θ] at the same movement position z are arranged in one direction, the pixels P[z, θ] corresponding to the line data L[z, θ] in the same transmission direction θ are arranged in a direction perpendicular to the one direction, and each pixel value is set according to the degree of abnormality of the generated line data L[z, θ].

According to this embodiment, it is possible to generate an image in which the state of the object to be detected can be observed from the observation result of the cross section of the biological tissue by the ultrasound.

In this embodiment, the control unit 41 derives line data that is composed of a plurality of brightness values arranged in the radial direction from the center of rotation for each rotation angle on the basis of the data obtained for the period for which the imaging core is rotated and moved. When the line data at the rotation angle θ of the probe 20 and the movement position z of the imaging core is defined as L[z, θ], the control unit 41 classifies the pattern of the line data L[z, θ], calculates the pixels P[z, θ] from the classification result, and calculates two-dimensional image data having z and θ as two axes. The control unit 41 displays the calculated two-dimensional image data.

According to this embodiment, the similarity between the vector for identifying the composition of the blood vessel or the stent and the vector composed of the line data is calculated for all of the lines, and a numerical value indicating the similarity is displayed as a pixel value, such as brightness, to visualize a composition pattern in the blood vessel.

As a modification example of this embodiment, the feature vector p may be a vector indicating a frequency distribution F[z, θ] of the intensity of the reflected wave in the transmission direction θ of the ultrasound which is calculated from the intensity value distribution A[z, θ].

Figure 10:
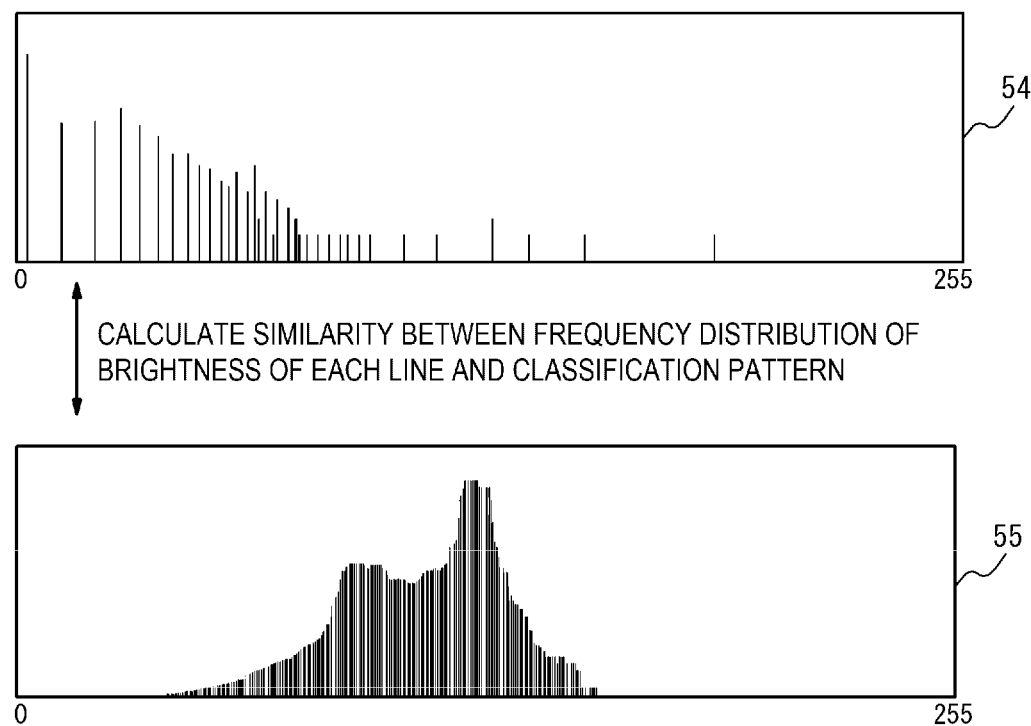
FIG. 10 is a diagram illustrating a modification example in which a frequency distribution of the brightness of the lines and the classification pattern are compared by the diagnosis assistance device.

In Step S6 of this modification example, the control unit 41 of the diagnosis assistance device 11 calculates the similarity between a frequency distribution 54 of the brightness of each line and a classification pattern 55 which is the pattern of the frequency with respect to brightness as illustrated in FIG. 10.

For example, the control unit 41 converts the brightness distribution 52 corresponding to the intensity value distribution A[1, 1] indicated by the line data L[1, 1] into the frequency distribution 54 of the brightness and calculates the similarity between the frequency distribution 54 and the classification pattern 55 of the stent which has been defined in advance. In addition, the control unit 41 converts the brightness distribution 52 corresponding to the intensity value distribution A[1, 2] indicated by the line data L[1, 2] into the frequency distribution 54 of the brightness and calculates the similarity between the frequency distribution 54 and the classification pattern 55 of the stent. Similarly, the control unit 41 converts the brightness distributions 52 corresponding to the intensity value distributions A[z, θ] indicated by other line data L[z, θ] into the frequency distributions 54 of the brightness and calculates the similarities between the frequency distributions 54 and the classification pattern 55 of the stent.

As a modification example of this embodiment, the feature vector p may be a vector indicating a change in the intensity value distribution A[z, θ] caused by a difference in the movement position z of the ultrasound transducer 25.

In Step S6 of the modification example, the control unit 41 of the diagnosis assistance device 11 calculates the similarity between the distribution of the amount of change in the brightness of each line between the cross-sectional images 50 and a classification pattern which is the pattern of the amount of change in the brightness with respect to the depth.

For example, the control unit 41 calculates the difference between the brightness distribution 52 corresponding to the intensity value distribution A[1, 1] indicated by the line data L[1, 1] and the brightness distribution 52 corresponding to the intensity value distribution A[2, 1] indicated by the line data L[2, 1] to calculate the change amount distribution of the brightness and calculates the similarity between the change amount distribution and the classification pattern of the stent which has been defined in advance. In addition, the control unit 41 calculates the difference between the brightness distribution 52 corresponding to the intensity value distribution A[2, 1] indicated by the line data L[2, 1] and the brightness distribution 52 corresponding to the intensity value distribution A[3, 1] indicated by the line data L[3, 1] to calculate the change amount distribution of the brightness and calculates the similarity between the change amount distribution and the classification pattern of the stent which has been defined in advance. Similarly, the control unit 41 calculates the difference between the intensity value distributions A[z, θ] indicated by other line data L[z, θ] in a time direction to calculate the change amount distribution of the brightness and calculates the similarities between the change amount distributions and the classification pattern of the stent.

In this modification example, the vector indicating the change in the intensity value distribution A[z, θ] caused by the difference in the movement position z of the ultrasound transducer 25 is an example of a vector that is calculated using the change in the intensity value distribution A[z, θ] caused by the difference in the movement position z of the ultrasound transducer 25. As another example of the vector, the feature vector p may be data from which noise has been removed by performing a filtering process as preprocessing such that the change in the intensity value distribution A[z, θ] caused by the difference in the movement position z of the ultrasound transducer 25 is reduced, instead of using the change in the intensity value distribution A[z, θ] caused by the difference in the movement position z of the ultrasound transducer 25 as it is.

As a modification example of this embodiment, the feature vector p may be a vector indicating a change in the intensity value distribution A[z, θ] caused by a difference in the transmission direction θ of the ultrasound.

In Step S6 of this modification example, the control unit 41 of the diagnosis assistance device 11 calculates the similarity between the change amount distribution of the brightness of each line between each line and an adjacent line and the classification pattern which is the pattern of the amount of change in the brightness with respect to the depth.

For example, the control unit 41 calculates the difference between the brightness distribution 52 corresponding to the intensity value distribution A[1, 1] indicated by the line data L[1, 1] and the brightness distribution 52 corresponding to the intensity value distribution A[1, 2] indicated by the line data L[1, 2] to calculate the change amount distribution of the brightness and calculates the similarity between the change amount distribution and the classification pattern of the stent which has been defined in advance. In addition, the control unit 41 calculates the difference between the brightness distribution 52 corresponding to the intensity value distribution A[1, 2] indicated by the line data L[1, 2] and the brightness distribution 52 corresponding to the intensity value distribution A[1, 3] indicated by the line data L[1, 3] to calculate the change amount distribution of the brightness and calculates the similarity between the change amount distribution and the classification pattern of the stent which has been defined in advance. Similarly, the control unit 41 calculates the difference between the intensity value distributions A[z, θ] indicated by other line data L[z, θ] in a spatial direction to calculate the change amount distribution of the brightness and calculates the similarities between the change amount distributions and the classification pattern of the stent.

In this modification example, the vector indicating the change in the intensity value distribution A[z, θ] caused by the difference in the transmission direction θ of the ultrasound is an example of a vector that is calculated using the change in the intensity value distribution A[z, θ] caused by the difference in the transmission direction θ of the ultrasound. As another example of the vector, the feature vector p may be data from which noise has been removed by performing a filtering process as preprocessing such that the change in the intensity value distribution A[z, θ] caused by the difference in the transmission direction θ of the ultrasound is reduced, instead of using the change in the intensity value distribution A[z, θ] caused by the difference in the transmission direction θ of the ultrasound as it is.

As described above, as a principle common to this embodiment and each modification example, the control unit 41 performs abnormality detection based on the distance between data items to detect, as an abnormal value, data having a behavior different from that of other data, that is, data that is not similar to other data, and expresses a difference in the distance between data with colors.

As a first step, the control unit 41 extracts features related to the object to be identified from the line data L[z, θ] and generates the feature vector p.

For example, there are the following methods for extracting the features from the line data L[z, θ].

(1) A method for calculating the distribution of the intensity values with respect to the depth, specifically, the brightness distribution 52 of each line (2) A method for calculating the distribution of the intensity values with respect to the frequency, specifically, the frequency distribution 54 of the brightness of each line (3) A method for calculating the distribution of (1) or (2) calculated from the amount of change between adjacent information items in the time direction, specifically, the change amount distribution of the brightness of each line between the cross-sectional images 50

(4) A method for calculating the distribution of (1) or (2) calculated from the amount of change between adjacent information items in the spatial direction, specifically, the change amount distribution of the brightness of each line between each line and an adjacent line (5) A method for calculating the distribution of (1), (2), (3), or (4) from which blood cell noise has been removed (6) A method for calculating the distribution of (1), (2), (3), (4), or (5) in which image quality has been adjusted so as to further improve the visibility of the object to be identified As a second step, the control unit 41 calculates the degree of abnormality of the feature vector p with respect to the object to be identified, using the identification vector q.

For example, there are the following methods for generating the identification vector q.

A method for holding the identification vector q as a fixed pattern for each object to be identified A method for generating the identification vector q using the "depth" or "intensity value" selected by the user In a case in which the feature vector p is similar to the identification vector q of the stent, "normal", that is, the degree of abnormality indicating the object to be identified is calculated. In a case in which the feature vector p is not similar to the identification vector q of the stent, "abnormal", that is, the degree of abnormality indicating an object other than the object to be identified is calculated.

As a third step, the control unit 41 assigns the degree of abnormality of the line data L[z, θ] to each pixel of the color map.

As illustrated in FIG. 9, in a case in which "normal", that is, the degree of abnormality indicating the object to be identified is calculated, the pixel intensity is set to a large value, and display is highlighted. In a case in which "abnormal", that is, the degree of abnormality indicating an object other than the object to be identified is calculated, the pixel intensity is set to a small value, and display is suppressed.

The object to be identified is not limited to the stent and may be another cluster such as a guide wire, a vessel wall, a calcified lesion, or a plaque. The degrees of abnormality for a plurality of clusters may be used together.

The brightness features of an image may be used together. For example, since a line including the stent has a large number of high-brightness components, the proportion of a high-brightness region to the entire line may be used. The proportion of brightness values equal to or greater than the threshold value to the frequency distribution of the brightness of each line may also be used. The threshold value may be a fixed value, a value input by the user, or a statistical value such as a mode value, an average value, or a variance of the line data L[z, θ].

Figure 11:
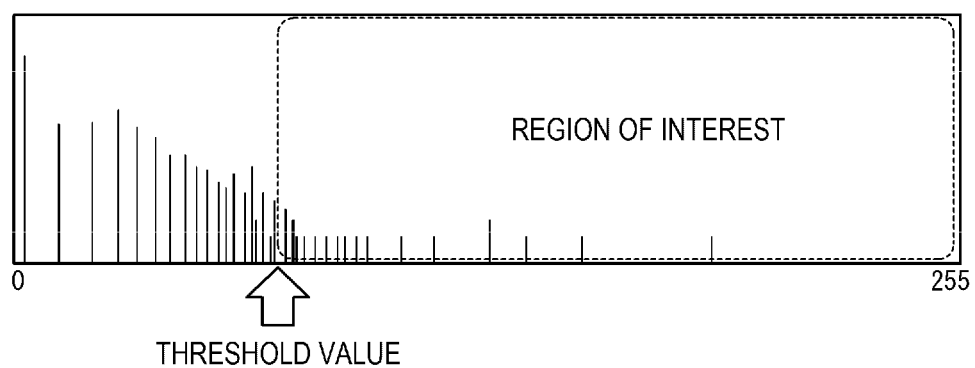
FIG. 11 is a diagram illustrating a modification example in which statistics of the brightness of the lines are used by the diagnosis assistance device.
Figure 12:
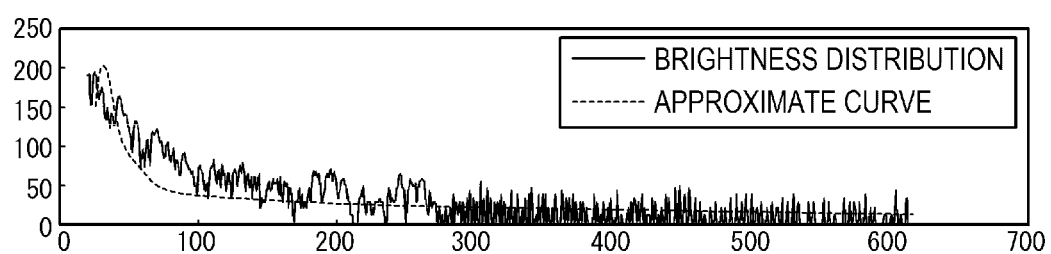
FIG. 12 is a diagram illustrating a modification example in which the slope of the maximum peak of the brightness distribution of the lines is used by the diagnosis assistance device.

The statistics of an image may also be used. For example, since the stent and the guide wire have different amounts of attenuation from the brightness peak, the variance of the high-brightness region of the line or the slope of an approximate curve of the brightness distribution 52 of the line may be used. As illustrated in FIG. 11, for the frequency distribution of the brightness, brightness variance in a region of interest equal to or greater than a threshold value may be used. The threshold value may be a fixed value, a value input by the user, or a value calculated from statistical characteristics such as a mode value, an average value, or a variance of the line data L[z, θ]. As illustrated in FIG. 12, an approximate curve may be calculated for the brightness distribution, and the slope of a curve passing through the maximum peak may be used.

As a modification example of this embodiment, the R value of each pixel of the detection image may be set according to the variance of the high-brightness region, the G value may be set according to the degree of abnormality with respect to the stent, and the B value may be set according to the proportion of the high-brightness region.

As a modification of this embodiment, at least two of the R value, G value, and B value of each pixel of the detection image may be set according to the degree of abnormality with respect to the stent, and different feature extraction methods, such as the above-described methods (1) and (2), may be applied to each of the set values.

The present disclosure is not limited to the above-described embodiment. For example, a plurality of blocks illustrated in the block diagram may be integrated, or one block may be divided. Instead of performing a plurality of steps described in the flowchart in time series according to the description, the steps may be performed in parallel or in a different order according to the processing capacity of the device that performs each step or as necessary. In addition, the present disclosure can be modified without departing from the scope of the present disclosure.

REFERENCE SIGNS LIST

10: Diagnosis assistance system
11: Diagnosis assistance device
12: Cable
13: Drive unit
14: Keyboard
15: Mouse
16: Display
17: Connection terminal
18: Cart unit
20: Probe
21: Drive shaft
22: Hub
23: Sheath
24: Outer tube
25: Ultrasound transducer
26: Relay connector
31: Scanner unit
32: Slide unit
33: Bottom cover
34: Probe connection portion
35: Scanner motor
36: Insertion hole
37: Probe clamp portion
38: Slide motor
39: Switch group
41: Control unit
42: Storage unit
43: Communication unit
44: Input unit
45: Output unit
50: Cross-sectional image
51: Polar coordinate space
52: Brightness distribution
53: Classification pattern
54: Frequency distribution
55: Classification pattern
60: Detection image

What is claimed is:

1. A diagnosis assistance device connectable to an ultrasound transducer that is positionable inside biological tissue and is axially movable along the biological tissue while radially outwardly transmitting ultrasound to determine a state of a stent, a guide wire, a vessel wall, a calcified lesion or plaque, the diagnosis assistance device comprising:
    a control unit configured to generate line data indicating an intensity value of a reflected wave from a reflection object, which is present in a transmission direction of the ultrasound, for each combination of an axial movement position of the ultrasound transducer and a transmission direction of the ultrasound with reference to an observation result of a cross section of the biological tissue by the ultrasound transducer;

a memory connected to the control unit and configured to store the generated line data indicating the intensity value of the reflected wave from the reflection object;

the control unit being configured to extract features of the generated line data as a feature vector and compare the feature vector to an identification vector identifying the stent, the guide wire, the vessel wall, the calcified lesion or the plaque;

the control unit being configured to calculate a degree of abnormality of the feature vector as a result of the comparison of the feature vector to the identification vector;

the control unit being configured to generate a detection image that includes pixels corresponding to the generated line data, with the pixels corresponding to the line data at a common axial movement position of the ultrasound transducer being arranged in one direction, the pixels corresponding to the line data in a common transmission direction being arranged in a direction perpendicular to the one direction, and each pixel value being set according to the degree of abnormality; and the memory being configured to store the detection image.

2. The diagnosis assistance device according to claim 1, further comprising an output interface that is operatively connectable to a display to output information about the detection image to the display to display the detection image.

3. A diagnosis assistance device operatively connectable to an ultrasound transducer that is movably positionable inside biological tissue to determine a state of a stent or a guide wire, the diagnosis assistance device comprising:

a control unit configured to generate line data indicating an intensity value of a reflected wave from a reflection object, which is present in a transmission direction of ultrasound, for each combination of a movement position of the ultrasound transducer that radially transmits the ultrasound while being moved inside the biological tissue and a transmission direction of the ultrasound with reference to an observation result of a cross section of the biological tissue by the ultrasound transducer and to generate a detection image which includes pixels corresponding to the generated line data and in which the pixels corresponding to the line data at a same movement position are arranged in one direction, the pixels corresponding to the line data in a same transmission direction being arranged in a direction perpendicular to the one direction, and each pixel value being set according to a degree of abnormality of the generated line data; and the control unit being configured to calculate the degree of abnormality by comparing a feature vector, obtained by extracting features of the generated line data, to an identification vector identifying the stent or guide wire, and the degree of abnormality of the feature vector being a similarity between the feature vector and the identification vector.

4. The diagnosis assistance device according to claim 3, wherein the control unit is configured to generate, as the line data, data indicating an intensity value distribution of the reflected wave in the transmission direction of the ultrasound.

5. The diagnosis assistance device according to claim 4, wherein the control unit is configured to refer to a cross-sectional image having a brightness value distribution corresponding to the intensity value distribution as the observation result of the cross section of the biological tissue.

6. The diagnosis assistance device according to claim 4, wherein the control unit is configured to convert the intensity value distribution into a distribution from a center of gravity of the cross section observed by the ultrasound transducer and is configured to generate data indicating the converted distribution as the line data.

7. The diagnosis assistance device according to claim 4, wherein the feature vector is a vector indicating the intensity value distribution.

8. The diagnosis assistance device according to claim 4, wherein the feature vector is a vector indicating a frequency distribution of intensity of the reflected wave in the transmission direction of the ultrasound which is calculated from the intensity value distribution.

9. The diagnosis assistance device according to claim 3, wherein the feature vector is a vector that is calculated using a change in the intensity value distribution caused by a difference in the movement position of the ultrasound transducer.

10. The diagnosis assistance device according to claim 4, wherein the feature vector is a vector that is calculated using a change in the intensity value distribution caused by a difference in the transmission direction of the ultrasound.

11. The diagnosis assistance device according to claim 3, wherein the control unit is configured to calculate the degree of abnormality of the feature vector using at least two different vectors as the identification vector and sets at least two of an R value, a G value, and a B value according to the degree of abnormality calculated using different vectors when setting a R value, a G value and a B value of each pixel as each pixel value of the detection image.

12. The diagnosis assistance device according to claim 3, wherein, when setting a R value, a G value and a B value of each pixel as each pixel value of the detection image, the control unit is configured to set one or two of the R value, the G value, and the B value according to statistics of the line data and sets at least one of the remaining values of the R value, the G value, and the B value according to the degree of abnormality of the feature vector.

13. The diagnosis assistance device according to claim 3, wherein the control unit is configured to calculate the degree of abnormality of the feature vector, using one identification vector for the stent and a different identification vector for the guide wire.

14. The diagnosis assistance device according to claim 3, wherein the control unit is configured to analyze the line data to detect a position of a blood cell region that is present in the transmission direction of the ultrasound and calculate a degree of abnormality of a vector, from which an element corresponding to the detected position has been excluded, as the degree of abnormality of the feature vector.

15. The diagnosis assistance device according to claim 3, wherein the control unit is configured to generate, as the detection image, a developed image in which the biological tissue is cut open along a movement direction of the ultrasound transducer.

16. A diagnosis assistance system comprising:
the diagnosis assistance device according to claim 3; and
a probe including the ultrasound transducer.

17. A diagnosis assistance method comprising:
radially transmitting ultrasound from an ultrasound transducer while the ultrasound transducer is moving inside a biological tissue in which a stent, a guide wire, a vessel wall, a calcified lesion or plaque is located;
generating line data indicating an intensity value of a reflected wave from a reflection object, which is present in a transmission direction of the ultrasound, for each combination of a movement position of the ultrasound transducer and the transmission direction of the ultrasound with reference to an observation result of a cross section of the biological tissue by the ultrasound transducer;

extracting features of the generated line data as a feature vector and comparing the feature vector to an identification vector identifying the stent, the guide wire, the vessel wall, the calcified lesion or the plaque;

calculating a degree of abnormality of the feature vector as a result of the comparison of the feature vector to the identification vector; and generating a detection image that includes pixels corresponding to the generated line data and in which the pixels corresponding to the line data at the same movement position are arranged in one direction, the pixels corresponding to the line data in the same transmission direction are arranged in a direction perpendicular to the one direction, and each pixel value is set according to the degree of abnormality of the feature vector.

* * * * *